US006732383B2

United States Patent
Cleary et al.

(10) Patent No.: US 6,732,383 B2
(45) Date of Patent: May 11, 2004

(54) GOGGLE WITH SIDE ARM FOR WEARING WITH A HELMET

(75) Inventors: Stephen P. Cleary, Waterbury, VT (US); Scott Oliver, Stowe, VT (US); Joseph R. McNeal, Hailey, ID (US); Christopher G. Miller, Draper, UT (US); Michael J. Roestel, Bountiful, UT (US)

(73) Assignee: The Burton Corporation, Burlington, VT (US)

( * ) Notice: Subject to any disclaimer, the term of this patent is extended or adjusted under 35 U.S.C. 154(b) by 0 days.

(21) Appl. No.: 10/008,357

(22) Filed: Dec. 3, 2001

(65) Prior Publication Data

US 2003/0101507 A1 Jun. 5, 2003

(51) Int. Cl.[7] .................................................. A61F 9/02
(52) U.S. Cl. ......................................................... 2/450
(58) Field of Search ............................ 2/10, 426, 452, 2/427, 428, 430–432, 438, 440, 451

(56) References Cited

U.S. PATENT DOCUMENTS

| 1,963,437 A | 6/1934 | Gray |
| 3,298,031 A | 1/1967 | Morgan |
| 3,582,194 A | 6/1971 | Liautand |
| 3,691,565 A | 9/1972 | Galonek |
| 3,713,732 A | 1/1973 | Gooch |
| 3,744,874 A | 7/1973 | McCarthy et al. |
| 3,781,560 A | 12/1973 | DeBurgh et al. |
| 3,782,810 A | 1/1974 | Marker |
| 3,783,452 A | 1/1974 | Benson et al. |
| 3,931,646 A | 1/1976 | Loughner |
| 4,077,068 A | 3/1978 | Anderson |
| 4,112,521 A | 9/1978 | Uke |
| 4,171,543 A | 10/1979 | Cressi |
| 4,176,410 A | 12/1979 | Matthias |
| 4,193,133 A | 3/1980 | Lailbach et al. |
| 4,240,718 A | 12/1980 | Wichers |
| 4,286,340 A | 9/1981 | Lathrop |
| 4,322,138 A | 3/1982 | Minart |
| 4,348,775 A | 9/1982 | Haslbeck |
| 4,367,561 A | 1/1983 | Solari |
| 4,391,498 A | 7/1983 | Rengstorff |
| 4,435,852 A | 3/1984 | Nesler |

(List continued on next page.)

FOREIGN PATENT DOCUMENTS

| EP | 0525238 B1 | 2/1993 |
| EP | 0732259 B1 | 9/1996 |
| EP | 0765805 B1 | 4/1997 |
| EP | 0898948 A1 | 3/1999 |
| WO | WO93/20786 | 10/1993 |
| WO | WO97/32550 | 9/1997 |
| WO | WO98/27902 | 7/1998 |
| WO | WO98/38544 | 9/1998 |

Primary Examiner—Katherine Moran
(74) Attorney, Agent, or Firm—Wolf, Greenfield & Sacks, P.C.

(57) ABSTRACT

A goggle having at least one side arm. The arms may be used to support the goggle on a wearer's head, and may be pivotally mounted to the goggle frame inward of an outermost portion of the goggle lens(es) or frame. The arms may reinforce the frame, in some cases, to help better retain a lens in the goggle frame. The arms may nest within a groove, cut out or other feature in the goggle frame, e.g., to enhance the aerodynamic performance or aesthetic appearance of the goggle. The arms may closely follow and/or continue a smooth natural contour of the goggle frame, e.g., to make the arms less obtrusive.

29 Claims, 2 Drawing Sheets

U.S. PATENT DOCUMENTS

| | | |
|---|---|---|
| 4,449,787 A | 5/1984 | Burbo et al. |
| 4,511,225 A | 4/1985 | Lipson |
| 4,556,995 A | 12/1985 | Yamamoto |
| 4,607,398 A | 8/1986 | Faulconer |
| 4,649,577 A | 3/1987 | Wiedner |
| 4,670,914 A | 6/1987 | Harris |
| 4,675,920 A | 6/1987 | Glasheen |
| 4,753,378 A | 6/1988 | Kastendieck et al. |
| 4,756,145 A | 7/1988 | Pelling |
| 4,787,731 A | 11/1988 | Rogers |
| 4,796,308 A | 1/1989 | Bourgeois |
| 4,804,261 A | 2/1989 | Kirschen |
| 4,852,189 A | 8/1989 | Duggan |
| 4,877,320 A | 10/1989 | Holden |
| 4,918,753 A | 4/1990 | Mermillod |
| 4,977,627 A | 12/1990 | Metcalfe et al. |
| 4,978,209 A | 12/1990 | Ohba |
| 5,000,558 A | 3/1991 | Blackstone |
| 5,005,965 A | 4/1991 | Walters |
| 5,009,496 A | 4/1991 | Holtan, Jr. et al. |
| 5,093,940 A | 3/1992 | Nishiyama |
| 5,148,550 A | 9/1992 | Hodgkinson et al. |
| 5,162,823 A | 11/1992 | Goldstein |
| 5,181,280 A * | 1/1993 | Zachry, Jr. .................. 2/452 |
| 5,189,447 A | 2/1993 | Oleson |
| 5,229,598 A | 7/1993 | Filipovich |
| 5,272,422 A | 12/1993 | Beaussant |
| 5,341,516 A | 8/1994 | Keim |
| 5,410,763 A | 5/1995 | Bolle |
| 5,444,876 A | 8/1995 | Cooper et al. |
| 5,495,623 A | 3/1996 | Leonardi |
| 5,511,251 A | 4/1996 | Brakas |
| 5,553,331 A | 9/1996 | Gentile |
| 5,555,571 A | 9/1996 | McCaffrey |
| 5,564,132 A | 10/1996 | Kuo |
| 5,587,747 A | 12/1996 | Bernheiser |
| 5,611,644 A | 3/1997 | Lutz |
| 5,636,388 A | 6/1997 | Hodges |
| 5,642,178 A | 6/1997 | Leonardi et al. |
| 5,657,493 A | 8/1997 | Ferrero et al. |
| 5,711,035 A | 1/1998 | Haslbeck |
| 5,742,946 A | 4/1998 | Garofalo |
| 5,752,280 A | 5/1998 | Hill |
| 5,790,230 A | 8/1998 | Sved |
| 5,802,621 A | 9/1998 | Chou |
| 5,802,622 A | 9/1998 | Baharad et al. |
| 5,815,235 A | 9/1998 | Runckel |
| 5,825,455 A | 10/1998 | Fecteau et al. |
| 5,845,341 A | 12/1998 | Barthold et al. |
| 5,857,221 A | 1/1999 | Geneve et al. |
| 5,867,841 A | 2/1999 | Chiang |
| 5,915,542 A | 6/1999 | Swiet |
| 5,956,778 A * | 9/1999 | Godoy .................. 2/428 |
| 5,969,787 A | 10/1999 | Hall et al. |
| 5,997,137 A | 12/1999 | MacIntosh, Jr. |
| 6,009,564 A | 1/2000 | Tackles et al. |
| 6,019,469 A | 2/2000 | Fecteau et al. |
| 6,036,310 A | 3/2000 | Moetteli |
| 6,038,706 A | 3/2000 | Seiler |
| 6,038,707 A | 3/2000 | Ryden et al. |
| 6,047,410 A * | 4/2000 | Dondero .................. 2/426 |
| 6,049,917 A | 4/2000 | Ryden |
| 6,076,196 A * | 6/2000 | Masumoto .................. 2/436 |
| 6,076,926 A | 6/2000 | Kostka |
| 6,098,207 A | 8/2000 | Burtin |
| 6,105,177 A * | 8/2000 | Paulson et al. .................. 2/431 |
| 6,119,276 A | 9/2000 | Newcomb et al. |
| 6,131,246 A | 10/2000 | Paulson et al. |
| 6,138,285 A | 10/2000 | Robrahn et al. |
| 6,138,286 A | 10/2000 | Robrahn et al. |
| 6,149,268 A | 11/2000 | Hall et al. |
| 6,151,720 A | 11/2000 | Chiang |
| 6,154,881 A | 12/2000 | Lee |
| 6,216,282 B1 | 4/2001 | Marzec |
| 6,233,342 B1 | 5/2001 | Fernandez |
| 6,247,811 B1 | 6/2001 | Rhoades et al. |
| 6,253,388 B1 | 7/2001 | Lando |
| 6,254,236 B1 | 7/2001 | Fecteau et al. |
| 6,282,727 B1 * | 9/2001 | Lindahl .................. 2/428 |

* cited by examiner us
GOGGLE WITH SIDE ARM FOR WEARING WITH A HELMET

FIELD OF INVENTION

This invention relates to eyewear.

BACKGROUND OF THE INVENTION

Goggles are widely used in a variety of applications, such as when skiing and snowboarding, working in hazardous conditions or with hazardous substances, and so on. In some cases, such as in skiing and snowboarding, goggles are worn both with and without a helmet. Most goggles are arranged so that they can be comfortably and effectively worn without a helmet. However, when these goggles are worn with a helmet, the sides of the goggles near the wearer's temples are often pulled away from the wearer's face, forming a gap between the goggles and the wearer's face where light, air or debris may enter.

For example, many ski and snowboard goggles have a curved frame that approximates the shape of the wearer's face. The head strap on these goggles is typically attached at the outermost sides of the goggle frame near the wearer's temples. This arrangement works well because the head strap is positioned near the wearer's temples and pulls the goggle frame back and in toward the wearer's head. However, when the goggles are used with a helmet, the head strap extends around the outside of the helmet and is pushed out away from the wearer's temples by the portion of the helmet at the sides of the wearer's face. This causes the strap to pull on the sides of the goggle at an angle directed more away from the wearer's head, and may cause the goggle to flex or splay and disengage from the wearer's face.

SUMMARY OF THE INVENTION

The inventors have appreciated that the problem of pull away of a goggle when wearing a helmet may be solved by supporting the goggle on a wearer's head via arms that are mounted to a goggle frame inward of an outermost extent of the frame on either side of the frame. This arrangement may direct the force of a head support for the goggle, such as an elastic head strap, at an angle that is more tangential to the curve of the wearer's head regardless of whether a helmet is worn or not. If a head strap is secured to the arms, the presence of a helmet on the wearer's head may cause the arms to swing away from the wearer's head and accommodate the change in angle that the strap pulls on the goggle. By swinging outward, the arms may maintain a force that is more approximately tangential to the goggle contour at the connection point of the arms to the goggle frame and help prevent the goggle sides from being pulled away from the wearer's face. Moreover, pivotally mounting the arms inward from the frame ends may shorten the effective lever arm that the strap may have to splay the goggle ends outward. The shortened lever arm effectively gives the head strap less ability to contort the goggle frame, and so less pull away of the goggle ends results.

In one illustrative embodiment of the invention, a goggle includes a frame having an opening, an outer periphery surrounding the opening, a top, a bottom and opposite sides. The outer periphery has a contour at the sides of the frame. A lens is constructed and arranged to mount to the goggle frame and to provide a viewing area for a wearer. At least one arm is pivotally mounted to the frame at a position inward of an outermost extent of the frame, and together with the frame forms a smooth contour at the outer periphery around a side of the frame from a top of the frame to the bottom. The at least one arm provides a support for the frame on a wearer's head, and a head support constructed and arranged to engage with a wearer's head is attached to the at least one arm.

In another illustrative embodiment, a goggle includes a frame having an opening, an outer periphery surrounding the opening, a top, a bottom and opposite sides. A lens is constructed and arranged to mount to the goggle frame and to provide a viewing area for a wearer. At least one arm is mounted to the frame at a position inward of an outermost extent of the frame and extends over a side of the frame from the top to the bottom. The at least one arm reinforces the frame to stiffen the frame at the sides in a top to bottom direction. A head support, constructed and arranged to engage with a wearer's head, is attached to the frame.

In another illustrative embodiment, a goggle includes a frame having an opening, an outer periphery surrounding the opening, a top, a bottom and opposite sides, the outer periphery having a contour at the sides of the frame. A face gasket is attached to the frame and arranged to mate with a wearer's face, and a lens is constructed and arranged to mount to the goggle frame and to provide a viewing area for a wearer. At least one arm is pivotally mounted to the frame at a position inward of an outermost extent of the frame, the at least one arm closely fitting a contour of the outer periphery around a side of the frame from a top of the frame to the bottom. The at least one arm is positioned forward of a rearward most portion of the face gasket. A head support, such as an elastic strap constructed and arranged to engage with a wearer's head, is attached to the at least one arm.

BRIEF DESCRIPTION OF THE DRAWINGS

Illustrative embodiments are described in connection with the following drawings, in which like numerals reference like elements, and wherein.

DETAILED DESCRIPTION

Illustrative embodiments of the invention are described below with reference to a goggle having a single lens, a face gasket, and an elastic head strap to secure the goggle on the wearer's head. It should be understood, however, that various aspects of the invention are not limited to the particular embodiments described, but instead may be used with any suitable goggle type, such as those with earstems in place of an elastic head strap, those without a face gasket, and/or those that have two or more lenses mounted to a frame.

Figure 1:
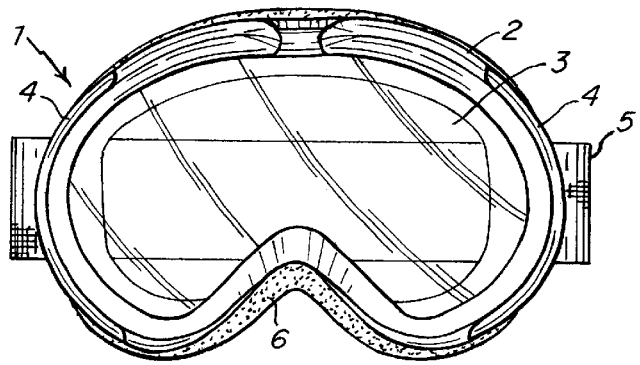
FIG. 1 shows a front view of a goggle in accordance with the invention.

FIG. 1 shows an illustrative embodiment of a goggle in accordance with the invention. In this embodiment, the goggle 1 includes a frame 2 having an opening for at least one lens 3. The goggle 1 also includes arms 4 that may be pivotally mounted at both sides of the frame 2. A head support 5, e.g., an elastic strap, may be secured to the arms 4 and used to hold the goggle 1 in place on a wearer's head. A face gasket 6 may be provided to give a close fit of the goggle 1 to the wearer's face. The arms 4 extend around the sides of the frame 2 from the top of the frame 2 to the bottom, and although not necessary, closely fit the contour of the outer periphery of the frame 2. In fact, in this embodiment, the arms 4 closely fit the contour of the frame and together with the frame form a smooth contour at the outer periphery around a side of the frame such that the arms 4 are difficult to distinguish from the frame 2 when viewed from the front, as in FIG. 1. By "smooth" in this context, it is meant that the frame 2 and arms 4 form a continuous shape without significant discontinuities, breaks or other irregularities in the shape. Thus, a "smooth" contour formed by the frame 2 and arms 4 may have any suitable surface appearance, texture or feel, such as a rough surface finish, e.g., a sandpaper-like surface, yet still be a smooth contour. A smooth contour of the frame 2 at the sides may make for a better appearance of the goggle, improve its aerodynamic performance, as well as help conceal the presence of the arms 4. That is, this aspect of the invention may make the arms unobtrusive, yet provide the goggle excellent fitting characteristics whether used with or without a helmet.

One aspect of the invention illustrated in FIG. 1 embodiment is that the arms 4 may be pivotally mounted to the frame at a position inward of the outermost extent of the lens 3 or the frame sides. This aspect of the invention may allow the arms to transfer the force of the head support 5 to the frame 2 so that the goggle is properly positioned relative to a wearer's face regardless of whether a helmet or other headgear is worn or not. By "inward" in this context, it is meant that the pivotal mounting is positioned in toward the center of the goggle 1 from the outer sides of the lens or frame, i.e., toward the wearer's nose. Conversely, "outward" in this context refers to a direction toward the sides away from the center of the goggle 1. By placing the retaining force of the head support 5 toward the center of the goggle 1, when the goggle 1 is used with a helmet, less force is exerted at the sides of the frame 1 that might cause the frame 2 to contort and pull away from the wearer's face.

Figure 2:
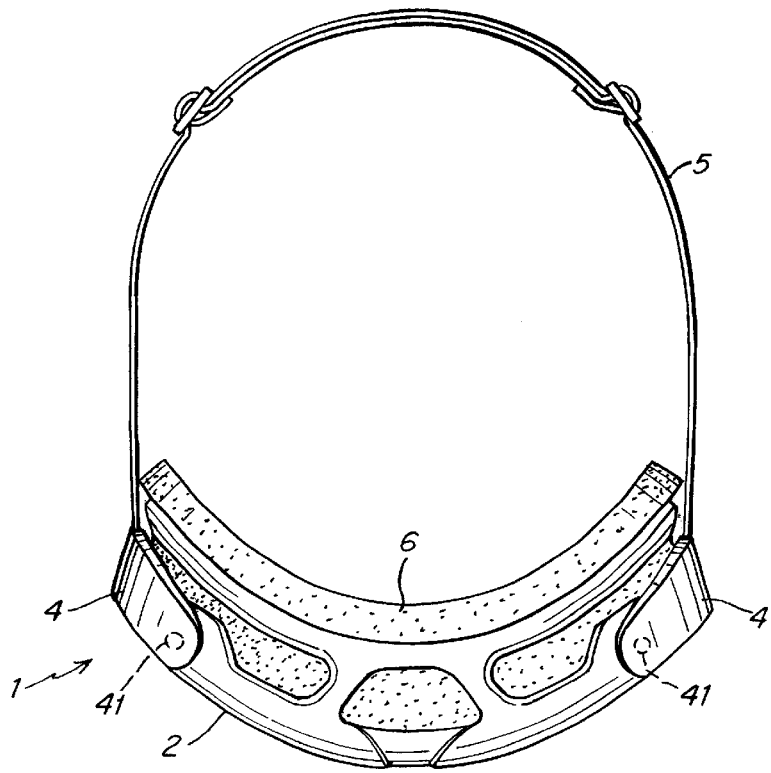
FIG. 2 shows a top view of the goggle of FIG. 1 with arms pivoted toward a wearer's face.
Figure 3:
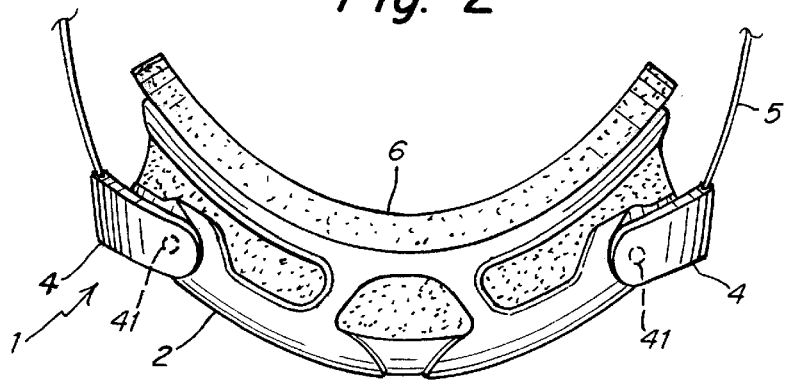
FIG. 3 shows a top view of the goggle of FIG. 1 with arms pivoted away from a wearer's face.

FIG. 2 shows a top view of the goggle 1 with the arms 4 rotated toward the wearer's head. This is the position that the arms 4 typically take when the goggle 1 is worn without a helmet or other headgear. The arms 4 are fitted closely to the frame 2 and keep the head support 5 close to the wearer's temples. FIG. 3 shows the arms 4 rotated away from the wearer's head in a position typical when the goggle 1 is worn with a helmet or other headgear. In this position shown in FIG. 3, the force of the head support 5 is transferred by the arms 4 to points inward on the frame 2. Thus, the presence of the extra thickness of the helmet near the wearer's temples is less likely to cause the sides of the goggle to pull away from the wearer's head as easily as would occur with a goggle that mounts a head strap in a conventional way. This may result because the force of the head support 5 is maintained more tangentially directed with respect to the shape of the wearer's head, and thus tends to keep the goggle in place.

One aspect of the invention illustrated in FIGS. 1–3 is that the arms 4 may be positioned forward of the face gasket 6. By "forward" in this context, it is meant that the arms 4 are positioned in front of the rearward most portion of the face gasket in a direction approximately parallel to the wearer's normal straight ahead line of sight, i.e., in a direction along the length of the wearer's head away from the back of the head. As can be seen in FIGS. 2 and 3, the arms 4 are positioned forward of the rearward most portion of the face gasket 6 regardless of the arms' position relative to the frame 2. According to this aspect of the invention, the arms 4 need not provide a side shield feature at the wearer's temples, and instead may be positioned out of the way for a helmet or other headgear that fits closely to the wearer's head and forward to approximately the temples, as is the case with some snow sports and motorcycle helmets. This is in contrast to some goggles that have pivotally mounted arms that have portions extending rearward of the face gasket or other rearward most portion of the frame 2. In these goggles, the arms may interfere with the portions of the helmet or other headgear near the wearer's temples, potentially preventing proper fit of the goggle.

Another aspect of the invention illustrated in the FIG. 1 embodiment is that the arms 4 extend around the sides of the frame 2 from the top to the bottom and reinforce the frame 1. Although the reinforcement of the arms 4 may provide additional stiffness or strength in any suitable way, the arms 4 may provide stiffness to the frame 2 in a top to bottom direction. For example, the ends of the arms 4 may be resiliently biased open to engage the frame 2, and when released, the arms 4 may engage the frame 2 with a compressive force that squeezes the top and bottom frame portions together. The additional stiffness provided by the arms 4 may help the frame 2 keep its shape and retain the lens 3 on the frame 2. Alternately, the additional stiffness provided by the arms 4 may allow the frame 2 to be made of a more flexible material or portions of the frame 2 to be more articulated than might be desirable without the arms. A more flexible frame material may make attachment of the lens on the frame 2 easier, e.g., because, with the arms 4 disengaged, top and bottom portions of the frame 2 may be more easily pulled apart in a top to bottom direction so that the lens 3 can be engaged in a groove or other mounting feature on the frame 2. Once the lens 3 is in place, the top and bottom portions may be urged back together and the arms 4 engaged to help hold the top and bottom portions and the lens in place. Making the frame 2 of a more flexible material may make the goggle 1 more comfortable to wear because of its ability to conform to the wearer's face. Articulated portions of the frame 2 may include hinges, linkages or other elements to allow the various frame portions to be manipulated when the arms 4 are disengaged. For example, the frame 2 may be split into top and bottom portions in a clamshell-type arrangement to receive a lens. The top and bottom portions may be connected by a hinge at one side that allows the top and bottom to be pivoted apart and the lens removed/inserted. Once the lens is mounted in place, the top and bottom portions may be rotated back together and locked in place by engaging an arm 4 on a side of the frame 2 opposite the hinge. Of course, other arrangements will occur to those of skill in the art, such as having two separable top and bottom frame portions that may be separated when the arms 4 are disengaged, and then locked together by the arms 4.

In another aspect of the invention, the arms 4 may include a stiffer material or otherwise be made more stiffly than the frame. By making the arms 4 more stiff than the frame 2, the arms may be made thinner, lighter, less obtrusive and/or provide additional reinforcement to the frame 2. The goggle 1 may also be made more lightweight overall since the relatively smaller arms 4 may provide structural integrity to the frame 2, allowing the frame to be made of lighter material and/or of a lighter construction, e.g., including weight saving cavities, voids, filler materials, etc. Arms 4 having an appropriate stiffness may also better transfer force of the head support 5 to the frame 2 without distortion. The arms 4 may be made of a stiff, but elastic material, a rigid, inelastic material, or in any other suitable fashion.

Figure 4:
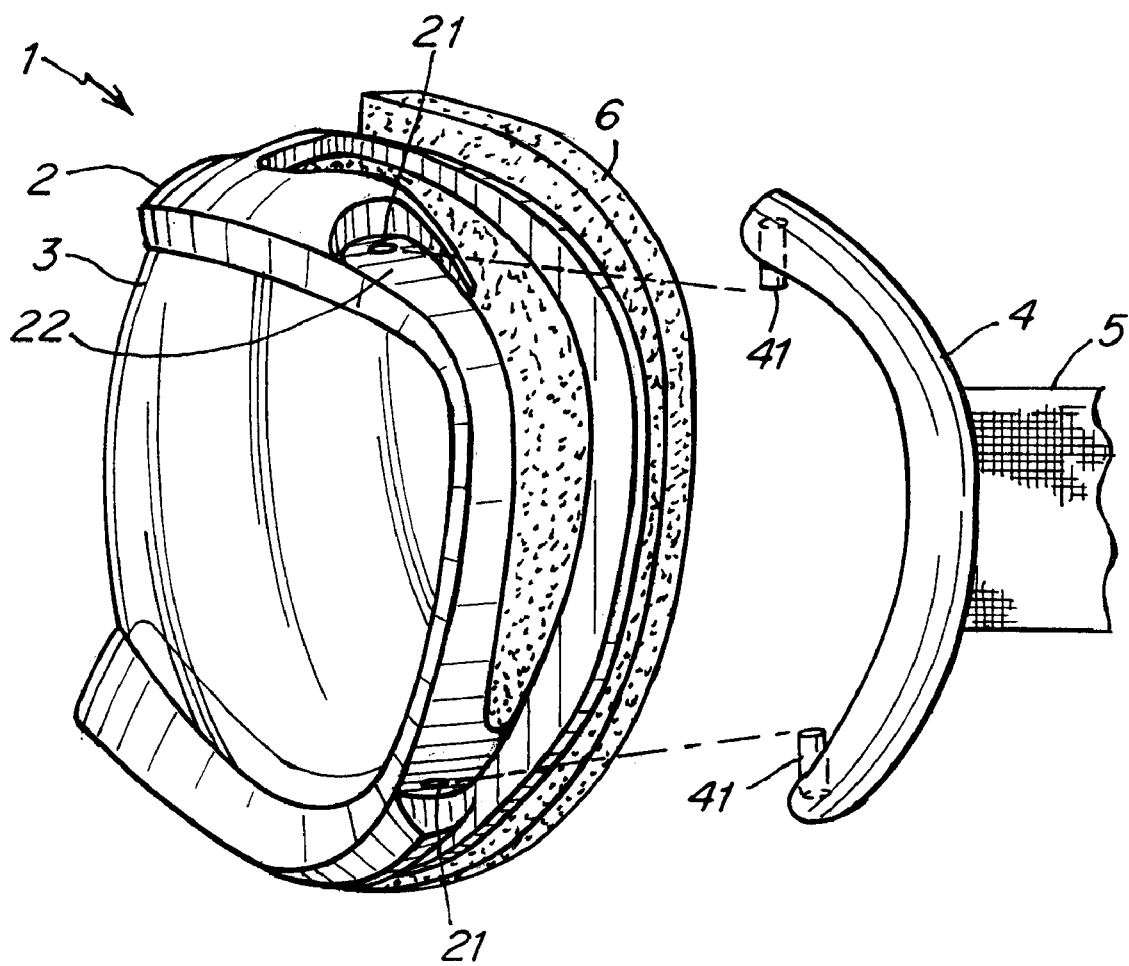
FIG. 4 shows a side view of the goggle of FIG. 1.

FIG. 4 shows a close-up side view of the FIG. 1 embodiment with an arm 4 detached from the frame 2. In this embodiment, the frame 2 has a groove 22, a cut out section, or other feature that receives the arcuate-shaped arm 4. The groove 22 may accept the arm 4 when the arm 4 is positioned nearest the wearer's face, or in any other position of the arm 4 relative to the frame 2. That is, although the groove 22 in this embodiment receives the arms 4 when positioned as shown in FIG. 2 and accepts only a portion of arms 4 when they are positioned away from the wearer's face as shown in FIG. 3, the groove 22 or other feature may receive all or part of the arms 4 in any position.

Pivot holes 21 are formed in the frame 2 to receive pivot pins 41 near the ends of the arm 4. When the pins 41 are engaged with the holes 21, force of the head support 5 is transferred from the arms to frame 2 at the holes 21 and the arms 4 may be free to rotate even when the head support 5 is supporting the goggle 1, i.e., the arms 4 may rotate on the frame 2 when the goggle is being worn. It should be understood that the illustrated embodiment of FIG. 4 is only one example, and that various modifications and alterations are contemplated. For example, the arms 4 may have pivot holes that engage with pivot pins on the frame, a screw, rivet, adhesive or other fastening arrangement may mount the arm to the frame, the arms may be made unitarily with the frame, and so on.

One aspect of the invention illustrated in FIG. 4 is that the arm 4 may be arranged to nest within a groove or other feature in the frame 2. This may allow the arm 4 to be made unobtrusive and/or to become part of the natural contour of the periphery of the frame 2. A close fit between the arm 4 and the frame 2 may reduce the overall size of the goggle 1, enhance the reinforcement that the arm 4 provides to the frame 2, enhance the aerodynamic performance of the goggle 1, and so on. Nesting of the arm 4 in a groove or other fitting of the arm within a cut out or other feature of the frame 2 may be provided in any suitable position of the arm 4 relative to the frame (if the arm 4 is made pivotable or otherwise movable on the frame) and regardless of how the arm 4 is secured to the frame 2. For example, the arm 4 may nest within a groove in the frame when the arm 4 is rotated in a position toward the wearer's face (e.g., as shown in FIG. 2) and/or when rotated in a position away from the wearer's face. Further, the arm 4 may nest in a groove or fit a contour of the frame whether made separate from the frame, or made unitarily as a single molded part with the frame.

Although in the embodiment above the goggle 1 includes a single lens 3, the goggle 1 may have two or more lenses arranged front to back (as with lenses having an insulating space between lenses to reduce fogging), side to side (as in typical spectacle-type goggles having one lens positioned in front of each eye) and/or other arrangements. Moreover, the frame need not have the particular shape shown in the figures, but instead may have any suitable shape, such as that found in safety glasses, welding goggles, and so on. That is, the frame may accommodate a single unitary lens, or separate lenses, and may have any suitable size, shape or other configuration. The frame also need not include a face gasket or wrap-around shape that closely conforms to the wearer's face, but instead may be formed much like ordinary spectacles.

The lens 3 may be mounted to the frame in any suitable way. In this embodiment, the frame 2 has a groove around its periphery to receive the lens 3, but as is well known in the art and not described in detail herein, the lens and/or frame may have any suitable features, materials or devices to help keep the lens mounted to the frame such as tabs, holes, pins, locking devices, slots, fasteners, adhesive, friction or snap fit, etc.

The goggle 1 may be held in place on a wearer's head in any suitable way. In the embodiment, above, the head support 5 includes an elastic strap, but the head support 5 may include other features, such as tension adjustment buckles, earstems that extend from the arms to engage the sides and/or ears of a wearer, snaps, clips, hook-and-loop fasteners or other devices to secure the arms to a helmet or other headgear, and so on. In the embodiment above, the head support 5 is fixed to arms 4 so that the head support 5 may not be adjusted in any way relative to the arms 4. However, it should be understood that the head support 5 may be secured to the arms 4 in any suitable way, e.g., so that the head support 5 may be moved relative to the arms 4 to adjust the tension of a head strap and/or to adjust a tilt of the goggle on the wearer's face. It is also possible that the head support 5 be secured directly to the frame 2 and not secured to the arms 4.

Having described certain embodiments of the present invention, various alterations, modifications, and improvements will readily occur to those skilled in the art. It should be understood that structure and composition of the goggle can vary from the illustrative embodiments described above. Therefore, such alterations, modifications and improvements are intended to be within the sprit and scope of the invention. Accordingly, the foregoing description is by way of example only, and not intended to be limiting.

What is claimed is:

1. A goggle comprising:

a frame having an opening, an outer periphery surrounding the opening, a top, a bottom and opposite sides, the outer periphery having a contour at the sides of the frame;

a lens constructed and arranged to mount to the goggle frame and to provide a viewing area for a wearer;

at least one arm pivotally mounted to the frame at a position inward of an outermost extent of the frame, the at least one arm together with the frame forming a smooth contour at the outer periphery around a side of the frame from the top of the frame to the bottom, the at least one arm providing a support for the frame on a wearer's head; and a head support attached to the at least one arm, the head support constructed and arranged to engage with a wearer's head.

2. The goggle of claim 1, wherein the frame includes a groove in the outer periphery at a side of the frame, and the at least one arm is constructed and arranged to nest within the groove.

3. The goggle of claim 1, wherein the at least one arm reinforces the side of the frame such that the lens is more positively held in place on the frame with the arm pivotally mounted to the frame than without the arm mounted to the frame.

4. The goggle of claim 1, wherein the outer periphery of the goggle at a side has a cut out portion, and the at least one arm is positionable to fit within the cut out portion, wherein the at least one arm continues a natural contour of the outer periphery when fit within the cut out portion.

5. The goggle of claim 1, further comprising a face gasket attached to the frame, the face gasket constructed and arranged to contact a wearer's face.

6. The goggle of claim 5, wherein the at least one arm is positioned forward of a rearward most portion of the face gasket.

7. The goggle of claim 6, wherein a portion of the at least one arm attached to the head support is forward of the face gasket when the arm is rotated to an inwardmost position toward the wearer's face.

8. The goggle of claim 1, wherein the at least one arm is more rigid than the side of the frame at which the at least one arm is mounted.

9. The goggle of claim 1, wherein the frame has two pivot holes at top and bottom portions of the frame near the side, and the at least one arm has an arcuate shape and pivot pins at opposite ends of the arm, the pivot pins engaging with corresponding pivot holes in the frame.

10. The goggle of claim 1, wherein the at least one arm and the frame together form a smooth contour around a side of the frame from the top to the bottom when the at least one arm is positioned at an inwardmost position toward the wearer's face.

11. A goggle comprising:
    a frame having an opening, an outer periphery surrounding the opening, a top, a bottom and opposite sides;
    a lens constructed and arranged to mount to the goggle frame and to provide a viewing area for a wearer;
    at least one arm mounted to the frame at a position inward of an outermost extent of the frame and extending over a side of the frame from the top to the bottom, the at least one arm reinforcing the frame to stiffen the frame at the sides in a top to bottom direction; and
    a head support attached to the frame, the head support constructed and arranged to engage with a wear's head, wherein the outer periphery of the goggle at a side has a cut out portion, and the at least one arm is positionable to fit within the cut out portion, wherein the at least one arm together with the frame forms a smooth contour at the outer periphery when fit within the cut out portion.

12. The goggle of claim 11, wherein the at least one arm is pivotally mounted to the frame at a position inward of the outermost extent of the frame.

13. The goggle of claim 11, wherein the head support is attached to the at least one arm.

14. The goggle of claim 11, wherein the frame includes a groove in the outer periphery at a side, and the at least one arm is constructed and arranged to nest within the groove.

15. The goggle of claim 11, wherein the at least one arm reinforces the side of the frame such that the lens is more positively held in place on the frame with the arm pivotally mounted to the frame than without the arm pivotally mounted to the frame.

16. The goggle of claim 11, further comprising a face gasket attached to the frame, the face gasket constructed and arranged contact a wearer's face.

17. The goggle of claim 16, wherein the at least one arm is positioned forward of a rearward most portion of the face gasket.

18. The goggle of claim 17, wherein a portion of the at least one arm attached to the head support is forward of the face gasket when the arm is rotated to an inwardmost position toward the wearer's face.

19. The goggle of claim 11, wherein the at least one arm is more rigid than the side of the frame at which the at least one arm is mounted.

20. The goggle of claim 11, wherein the frame has two pivot holes at top and bottom portions of the frame near the side, and at least one arm has an arcuate shape and pivot pins at opposite ends of the arm, the pivot pins engaging with corresponding pivot holes in the frame.

21. The goggle of claim 11, wherein the frame and the at least one arm together form a smooth contour from the top to the bottom at a side of the frame when the at least one arm is at an inwardmost position toward the wearer's face.

22. A goggle comprising:
    a frame having an opening, an outer periphery surrounding the opening, a top, a bottom and opposite sides, the outer periphery having a contour at the sides of the frame;
    a face gasket attached to the frame and arranged to mate with a wearer's face;
    a lens constructed and arranged to mount to the goggle frame and to provide a viewing area for a wearer;
    at least one arm pivotally mounted to the frame at a position inward of an outermost extent of the frame, the at least one arm closely fitting the contour of the outer periphery around a side of the frame from the top of the frame to the bottom, the at least one arm being positioned forward of a rearward most portion of the face gasket when the at least one arm is rotated to an inwardmost position; and
    a head support attached to the at least one arm, the head support constructed and arranged to engage with a wearer's head.

23. The goggle of claim 22, wherein the frame includes a groove in the outer periphery at a side, and the at least one arm is constructed and arranged to nest within the groove.

24. The goggle of claim 22, wherein the at least one arm reinforces the side of the frame such that the lens is more positively held in place on the frame with the arm pivotally mounted to the frame than without the arm pivotally mounted to the frame.

25. The goggle of claim 22, wherein the outer periphery of the goggle at a side has a cut out portion, and the at least one arm is positionable to fit within the cut out portion, wherein the at least one arm together with the frame forms a smooth contour at the outer periphery when fit within the cut out portion.

26. The goggle of claim 22, wherein a portion of the at least one arm where the head support is attached is forward of the face gasket when the arm is rotated to an inwardmost position.

27. The goggle of claim 22 wherein the at least one arm is more rigid than the side of the frame at which the at least one arm is mounted.

28. The goggle of claim 22, wherein the frame has two pivot holes at top and bottom portions of the frame near the side, and at least one arm has an arcuate shape and pivot pins at opposite ends of the arm, the pivot pins engaging with corresponding pivot holes in the frame.

29. The goggle of claim 22, wherein the frame and the at least one arm together form a smooth contour from the top to the bottom at a side of the frame when the arm is rotated to an inwardmost position toward the wearer's face.

* * * * *